US00PP30760P3

(12) United States Plant Patent
Noh et al.

(10) Patent No.: US PP30,760 P3
(45) Date of Patent: Jul. 30, 2019

(54) GRAPEVINE PLANT NAMED 'HONGJU'

(50) Latin Name: *Vitis vinifera*
Varietal Denomination: Hongju

(71) Applicant: The Rural Development Administration, Republic of Korea, Jeollabuk-do (KR)

(72) Inventors: Jeong-Ho Noh, Jeollabuk-do (KR); Kyo-Sun Park, Jeollabuk-do (KR); Hae-Keun Yun, Daegu (KR); Jong-Chul Nam, Daegu (KR); Sung-Min Jung, Jeollabuk-do (KR); Youn Young Hur, Jeollabuk-do (KR); Hae-Sung Hwang, Jeollabuk-do (KR)

(73) Assignee: The Rural Development Administration, Republic of Korea (KR)

( * ) Notice: Subject to any disclaimer, the term of this patent is extended or adjusted under 35 U.S.C. 154(b) by 0 days.

(21) Appl. No.: 15/732,718

(22) Filed: Dec. 19, 2017

(65) Prior Publication Data

US 2019/0191611 P1 Jun. 20, 2019

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 5/0812; A01H 5/08; A01H 5/00; A01H 5/02; A01H 6/88
See application file for complete search history.

(56) References Cited

FOREIGN PATENT DOCUMENTS

| | | |
|---|---|---|
| CN | 20162385.9 | 12/2016 |
| CN | 20162385.9 | 1/2017 |
| CN | 20162385.9 | 6/2017 |
| KR | 2014-327 | 6/2014 |

OTHER PUBLICATIONS

KSVS Korea Seed & Variety Service PVP Right application for Hongju Seedless Jun. 15, 2014, retrieved on Nov. 7, 2018, retrieved from the Internet at http://www.seed.go.kr/english/function/systern_05_view.jsp?appl_idty=110134, one page. (Year: 2014).*
National Institute of Horticulture & Herbal Science, RDA. Annual Report 2013, Officieal Record No. 11-1390804-000493-10, cover page and p. 37. (Year: 2013).*
Roh et al. 'Hongju':A Seedless Table Grape Cultivar. HortScience 53(12):1-2 2018. (Year: 2018).*

* cited by examiner

*Primary Examiner* — June Hwu
(74) *Attorney, Agent, or Firm* — Knobbe, Martens, Olson & Bear, LLP

(57) ABSTRACT

A new and distinct grapevine variety 'HONGJU' is by characterized a late harvest date, the production of dense clusters of seedless, ovoid, grey red berries.

9 Drawing Sheets

Latin name of the genus and species claimed: *Vitis vinifera.*

Variety denomination: 'HONGJU'.

BACKGROUND AND SUMMARY OF THE INVENTION

This application relates to the discovery and asexual propagation of a new and distinct variety of grapevine, 'Hongju', as herein described and illustrated. The new variety was first selected in the Republic of Korea in 2006. A second selection of the variety took place in 2007 and the process of regional adaptability took place from 2008-2013. The variety was originated by controlled crossing.

The new variety 'Hongju' is characterized by a late harvest date, the production of seedless, ovoid, grey red berry and a dense cluster of berries.

The seed parent is the varietal selection 'Italia' and the pollen parent is 'Perlon'. The parent varieties were first crossed in Jun. 5, 1996. The date of first sowing was Feb. 17, 1997, and the date of first flowering was Jun. 8, 2000.

The new variety 'Hongju' was first asexually propagated in Feb. 2, 2008 in Imok-dong, Jangan-gu, Suwon-si, Gyeonggi-do, in the Republic of Korea by Jeong-Ho Noh, Kyo-Sun Park, Hae-Keun Yun, Jong-Chul Nam, Sung-Min Jung, Youn Young Hur, Hae-Sung Hwang using hardwood cuttings.

The new variety 'Hongju' differs from its seed parent 'Italia' in that the new variety 'Hongju' is very vigorous with berries having an ovoid shape, no particular flavor and no seeds compared to "Italia" which has vigorous growth, berries having seeds, a cylindrical shape, and muscat flavor. The new variety 'Hongju' also differs from its seed parent 'Italia' in that the new variety 'Hongju' has a dense cluster of berries with a later date of bud burst of about May 3$^{rd}$ and later date of full bloom of about June 8$^{th}$ compare to a date of bud burst of about April 25$^{th}$ and full bloom date of about June 5$^{th}$ for 'Italia'. The new variety 'Hongju' also differs from its seed parent 'Italia' in that the new variety 'Hongju' has an approximate date of maturity of October 1$^{st}$, with about 113 days of growth to maturity, compared to an approximate date of maturity of September 20$^{th}$, with about 104 days of growth to maturity, for 'Italia'.

The new variety 'Hongju' differs from its pollen parent 'Perlon' in that the fruit of the new variety has a weak muscat scent compared to no scent for 'Perlon'.

The new variety 'Hongju' differs from 'Campbell early' in that 'Hongju' has seedless berries with an ovoid shape, compared to the seeded, globe-shaped berries of 'Campbell early'. The berries of the new variety 'Hongju' also have a grey red skin and no particular flavor compared to the blue black skin color of the berries of 'Campbell early', which also have a foxy flavor. The new variety 'Hongju' also differs from 'Campbell early' in that it has a later date of bud burst of around May 3th and a later date of full bloom of about June 8$^{th}$, compared to a date of bud burst of around April 22$^{nd}$ and date of full bloom of about June 5$^{th}$ for 'Campbell early'. The new variety 'Hongju' has an approximate date of maturity of October 1$^{st}$ with 113 days of growth and maturity, compared to an approximate date of maturity of September 2$^{nd}$ and 89 days of growth and maturity for 'Campbell early'.

The new 'Hongju' variety has been shown to maintain its distinguishing characteristics through successive asexual propagations by, for example, cuttings.

Variations of the usual magnitude from the characteristics described herein may occur with changes in any of a variety of factors such as growing conditions, irrigation, fertilization, pruning, management and climatic variation.

BRIEF DESCRIPTION OF THE DRAWING

The accompanying color photographic illustrations are of an eight year old plant and were taken shortly after the fruit was picked and the colors are as nearly true as is reasonably possible in a color representation of this type.

DETAILED DESCRIPTION

Figure 1:
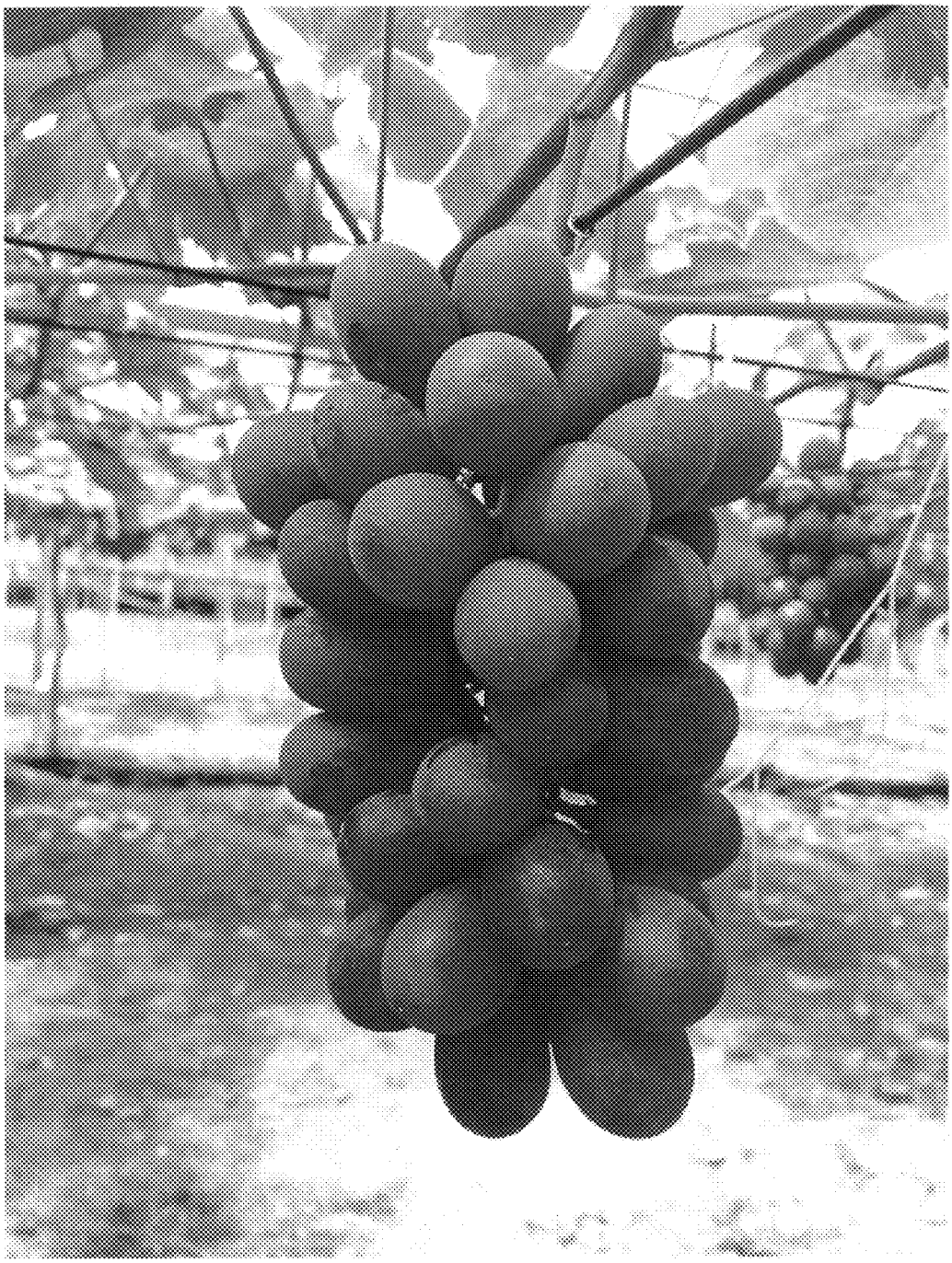
FIG. 1 shows a cluster of the fruit of the new variety 'Hongju'.
Figure 2:
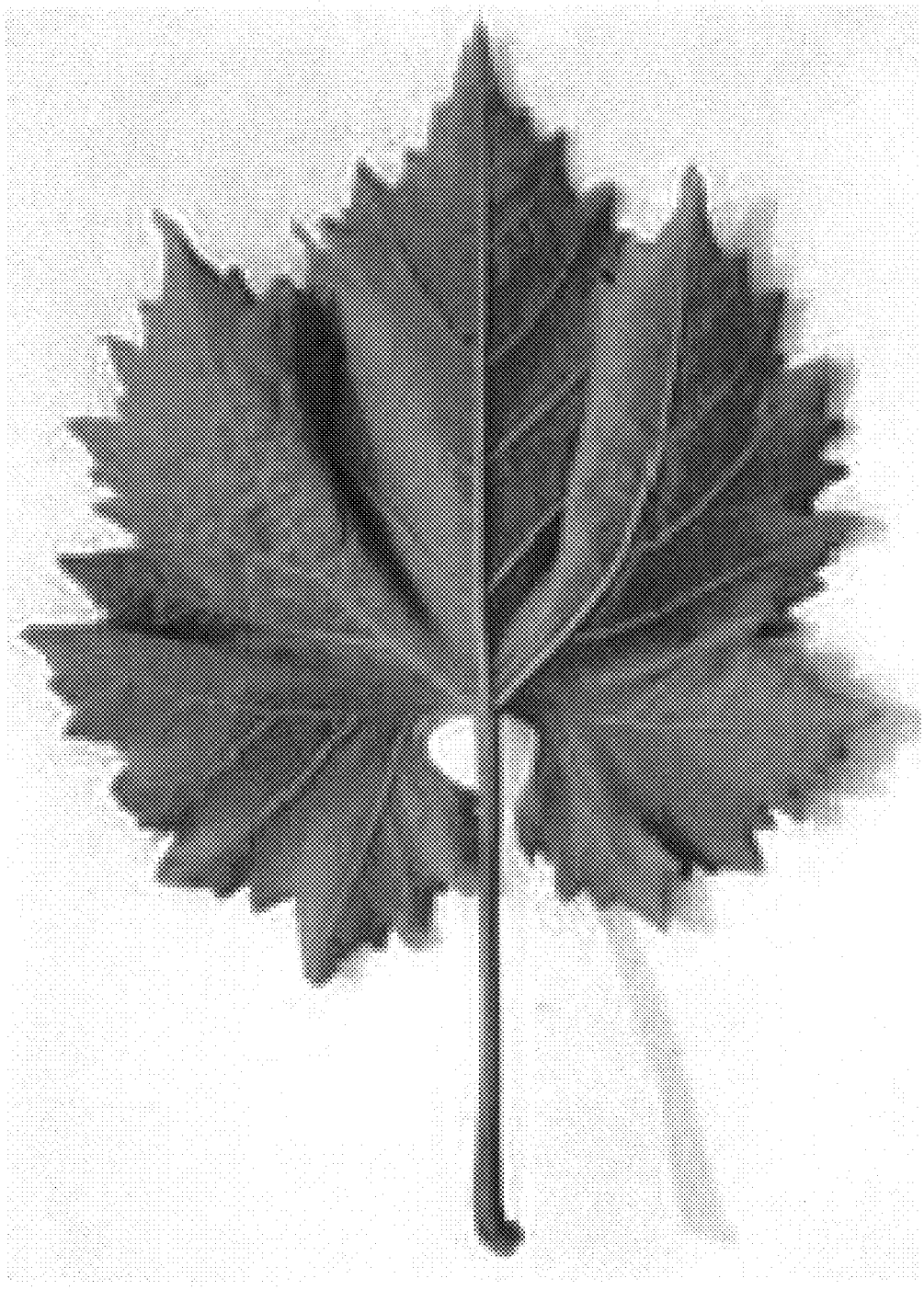
FIGS. 2 and 3 show typical specimens of the foliage of the new variety 'Hongju'.
Figure 3:
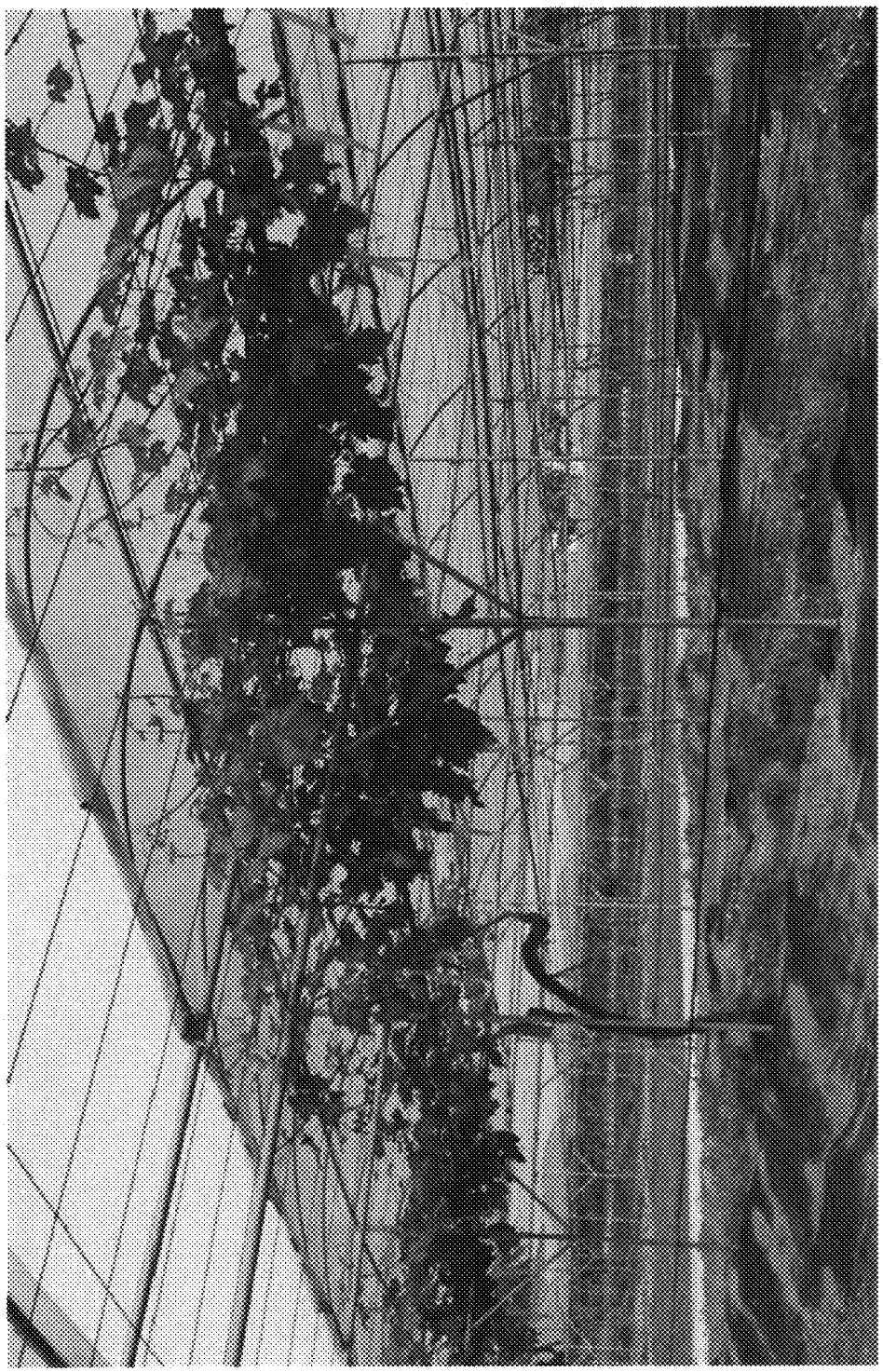
Figure 4:
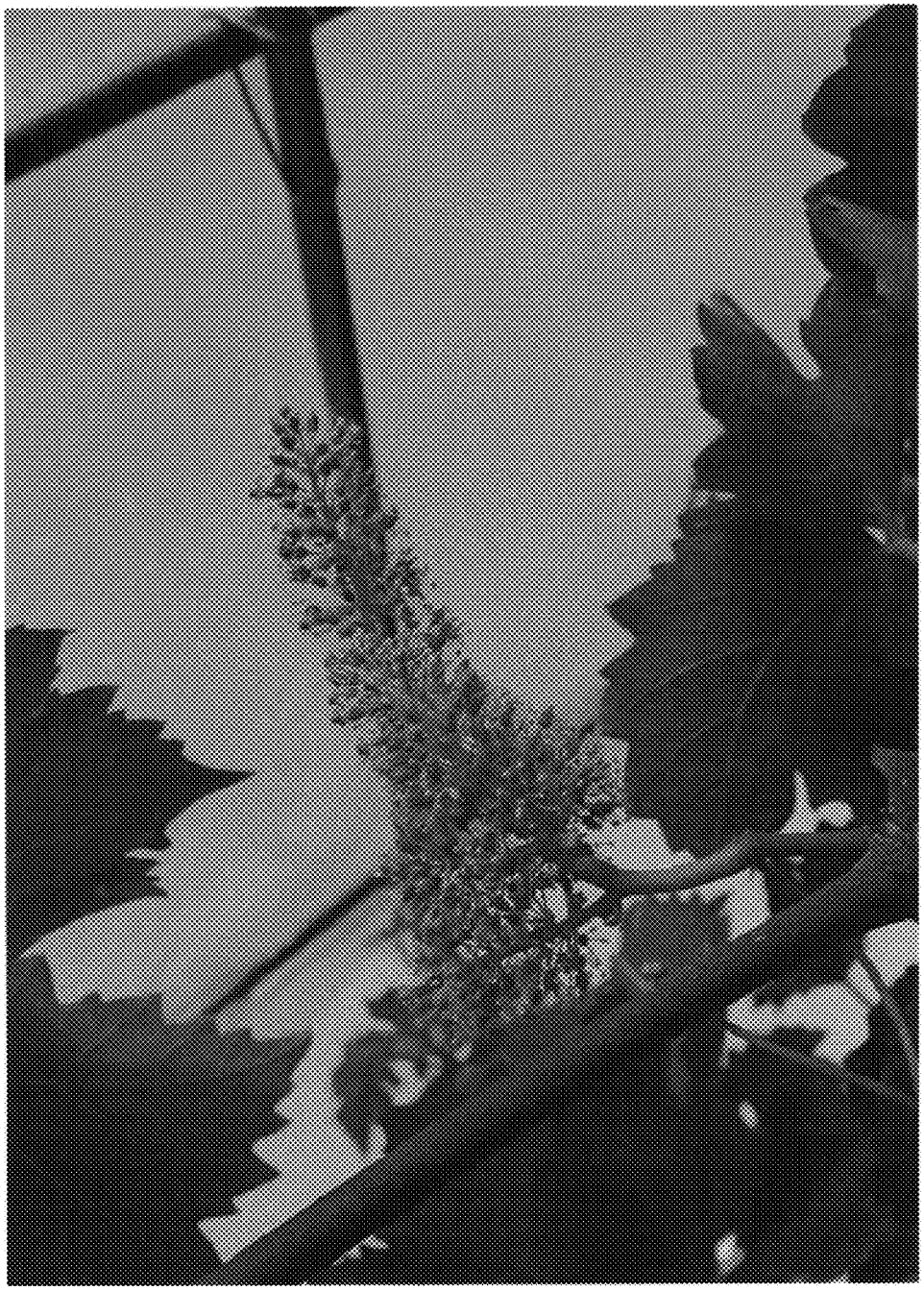
FIG. 4 shows typical specimens of the inflorescence of the new variety 'Hongju'.
Figure 5:
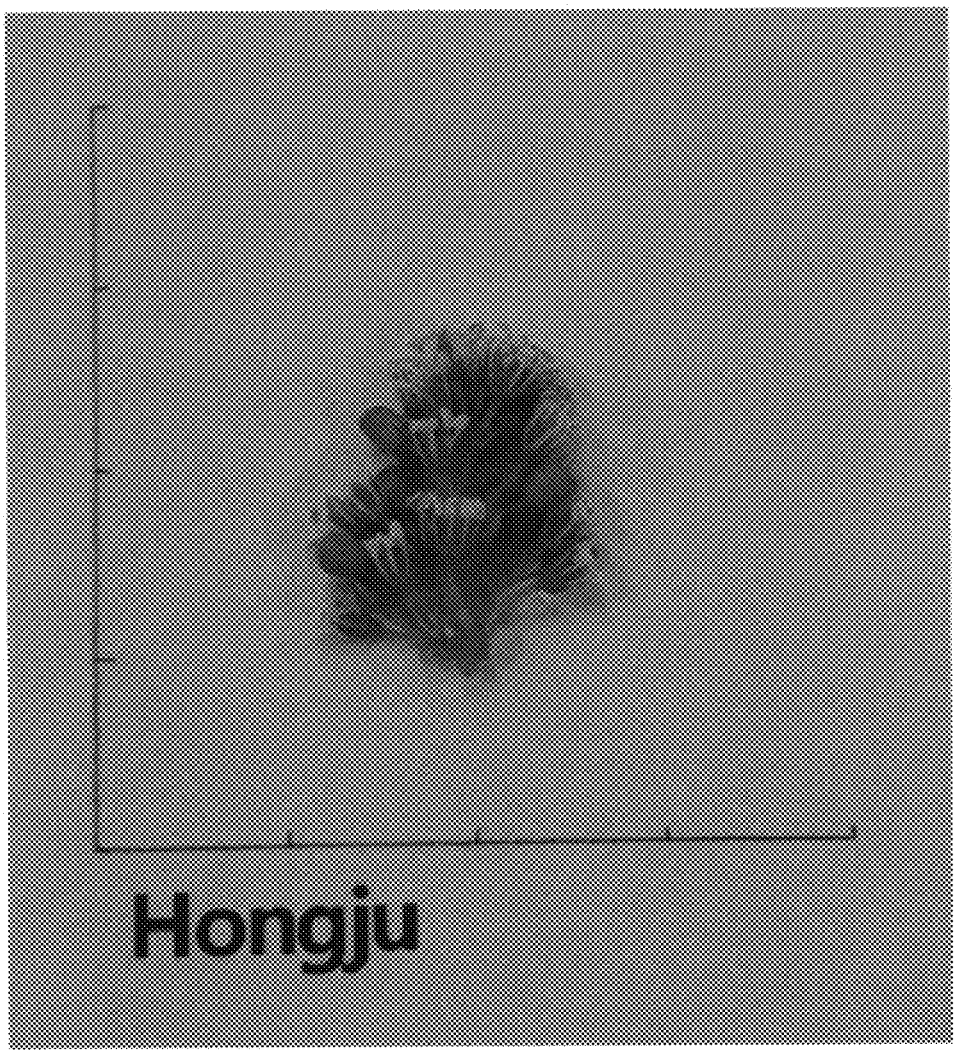
FIG. 5 shows typical specimens of the spikelet on the inflorescence of the new variety 'Hongju'.
Figure 6:
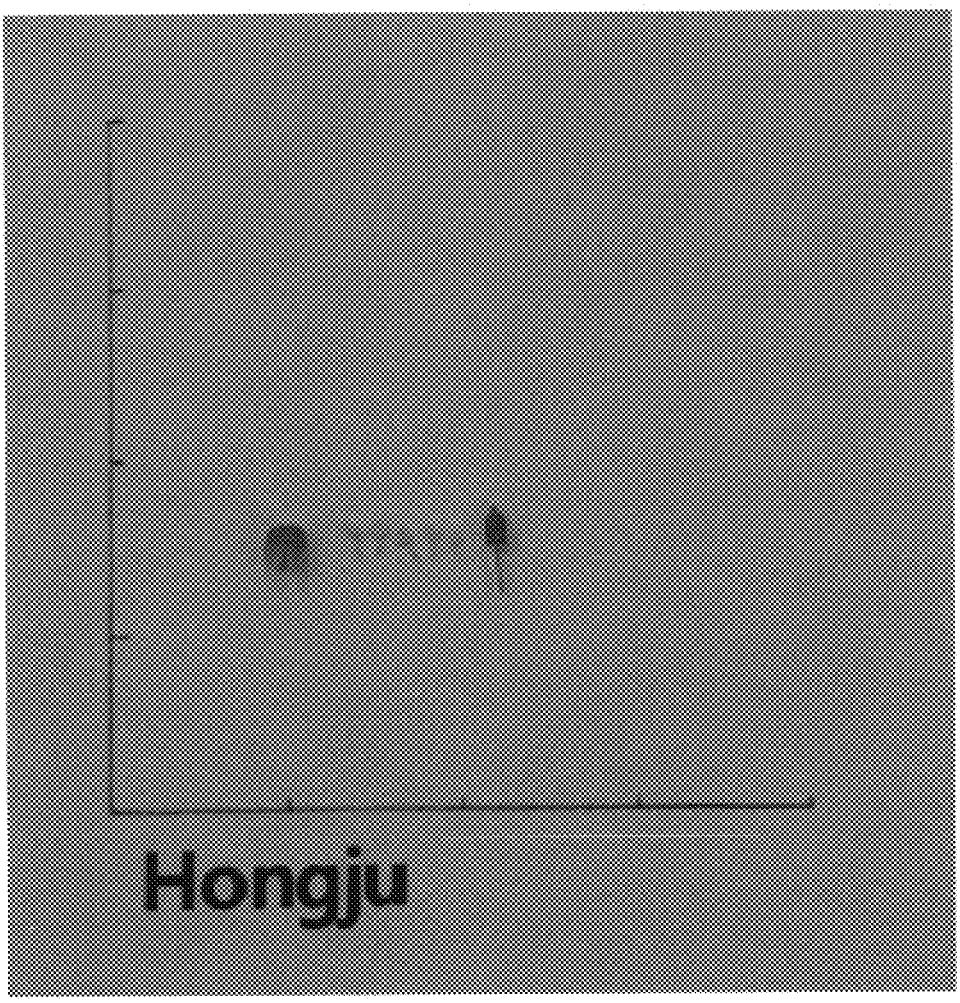
FIG. 6 shows typical specimens of the flower anatomy of the new variety 'Hongju'.
Figure 7:
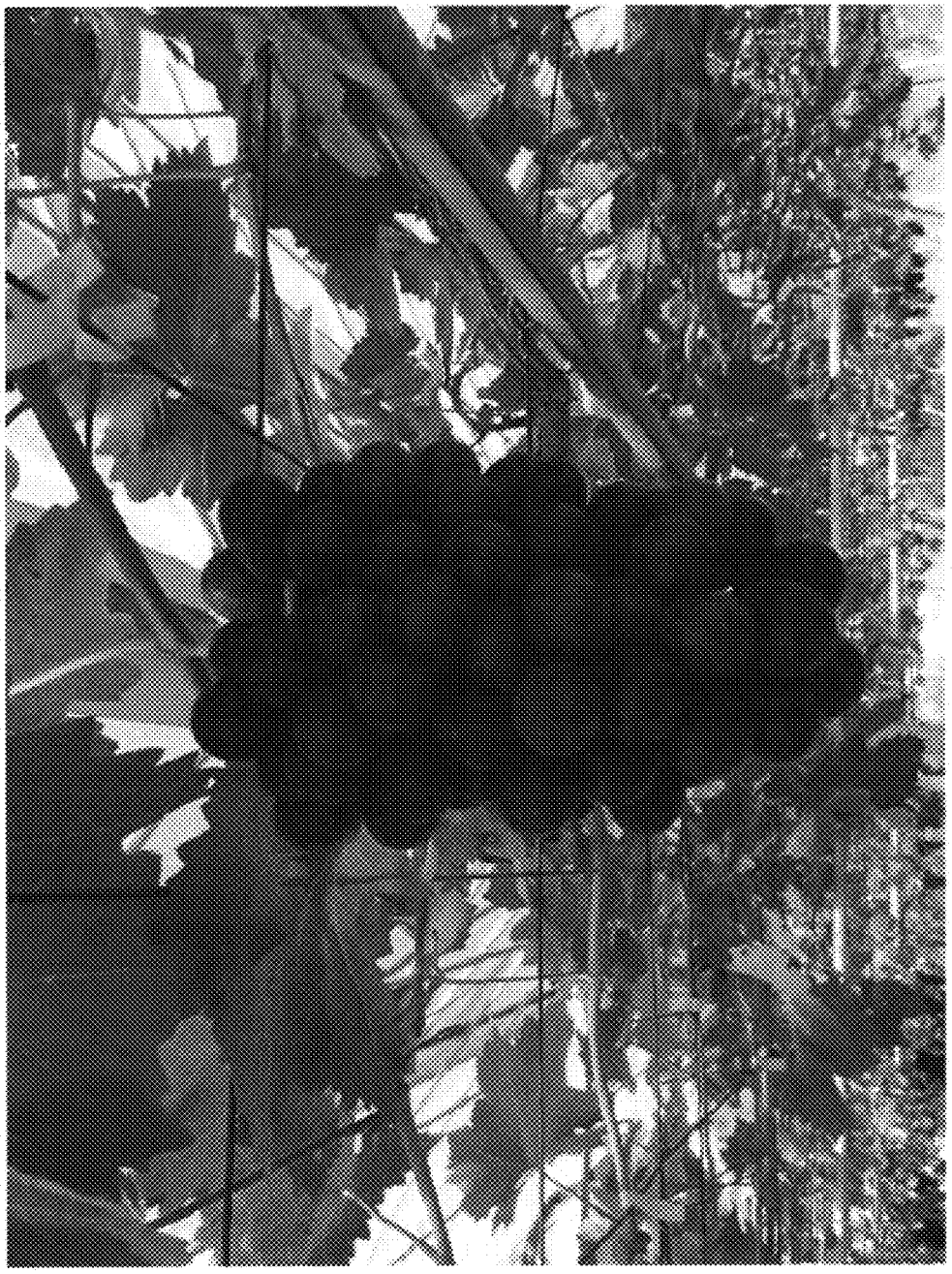
FIG. 7 shows a cluster of the fruit with foliage of the new variety 'Hongju'.
Figure 8:
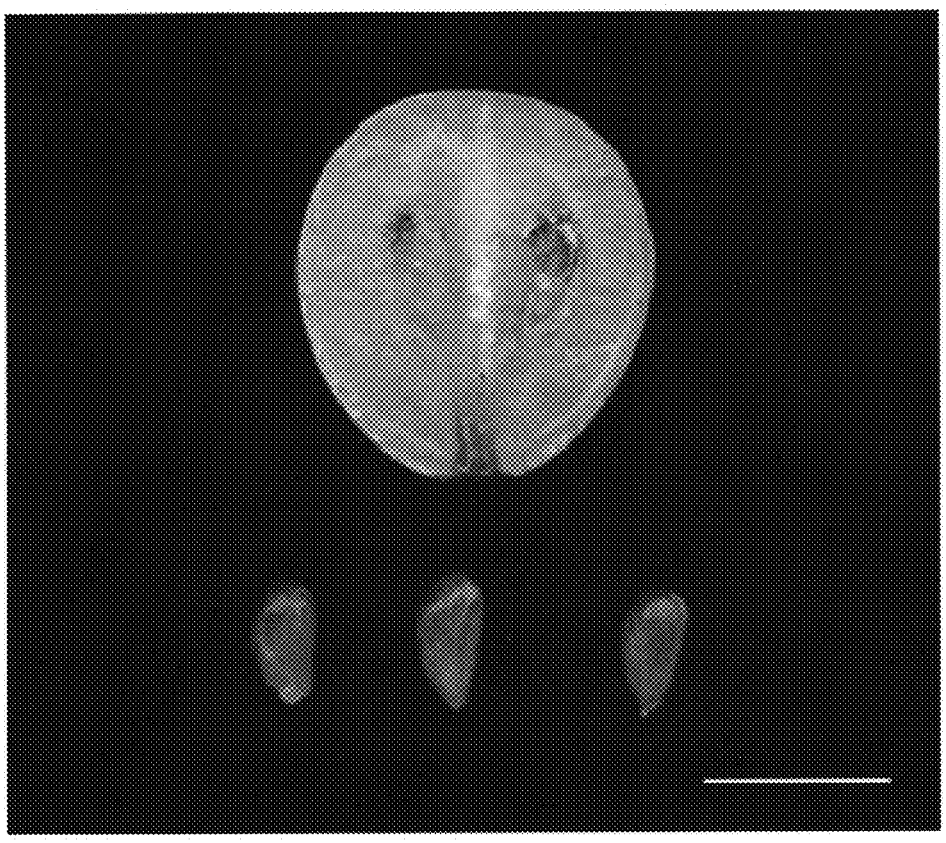
FIG. 8 shows a cross section of the berry of the new variety 'Hongju'.
Figure 9:
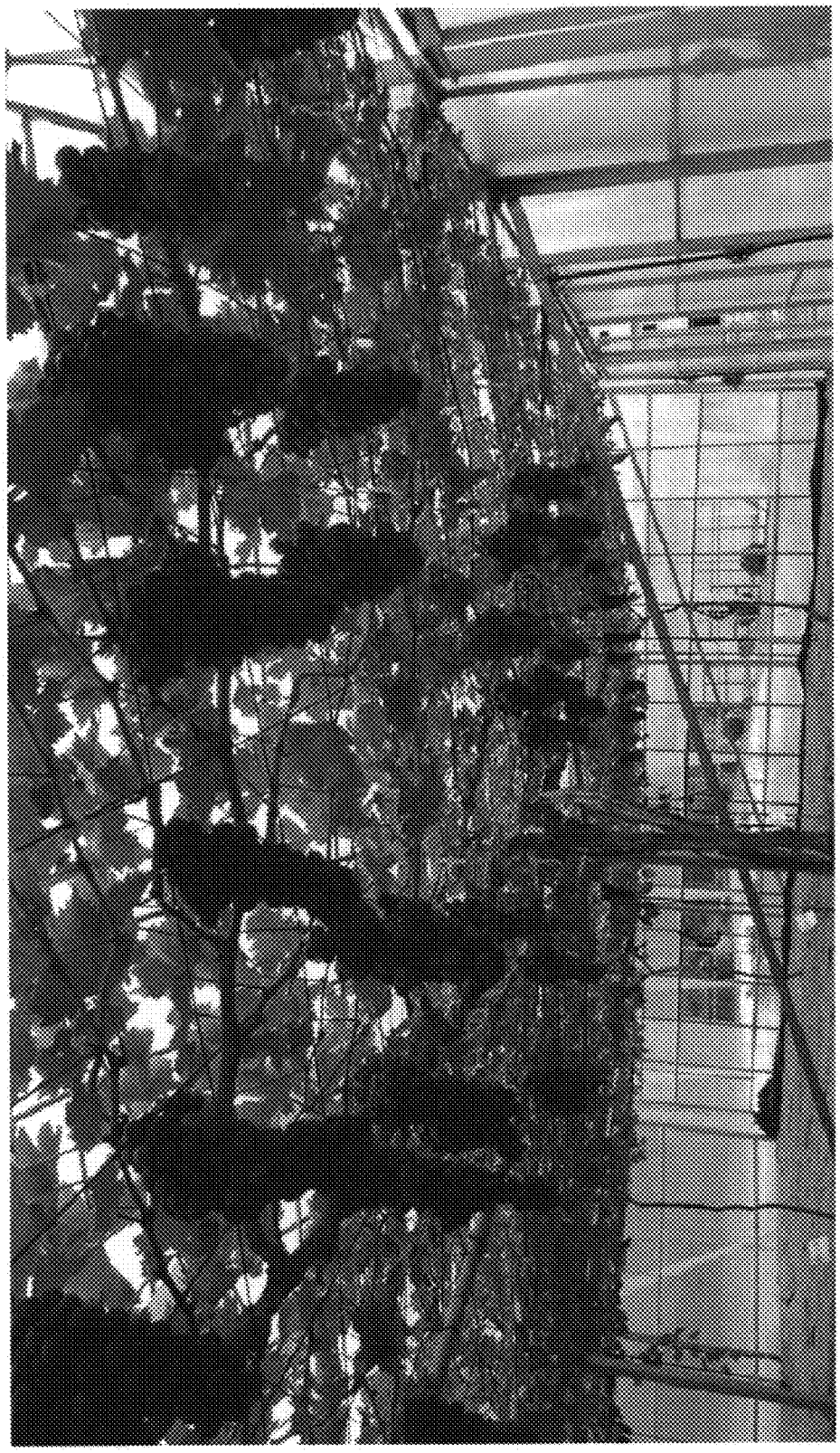
FIG. 9 shows a group clusters with foliage of the fruit of the new variety 'Hongju'.

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, Fifth Edition.

Many of the descriptive values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to four year old 'Hongju' plants grown in the Republic of Korea during 1997-2005, and is believed to apply to plants of the variety grown under similar conditions of soil and climate elsewhere.

VINE

General: (Measurements taken on an eight year old plant).

*Vigor.*—Vigorous.

*Productivity.*—Productive.

*Crop load.*—Approximately 2,000 Kg per 10a.

*Hardiness.*—Average, typical of *Vitis vinifera.*

*Susceptibility and resistance.*—The foliage is moderately susceptible to downy mildew (*Plasmopara viticola* Berl. & de Toni). However, powdery mildew (*Erysiphe necator* Schw.) on the vines during the cultivation period was not observed.

Trunk:

*Diameter of a* 10-*year old vine at* 30 *cm above the soil line.*—Approximately 23.5 cm.

*Surface texture.*—Rough.

*Color of inner bark.*—About Greyed-Orange 165B and Greyed-Orange 165C.

SHOOTS

*Attiude.*—Erect.

*Color of ventral sides of internode.*—About Greyed-Orange N167 B & C.

*Color of dorsal sides of internode.*—About Greyed-Orange N167 A & B.

*Color of ventral side of nodes.*—About Greyed-Orange 166 B & C.

*Color of dorsal side of nodes.*—About Greyed-Orange 166 B & C.

*Density of erect hairs on internode.*—Sparse.

Young shoot:

*Form of tip.*—Half open.

*Color.*—About Yellow-Green 144B.

*Distribution of anthocyanin coloration of tip.*—Absent.

*Intensity of anthocyanin coloration of tip.*—Absent.

*Density of prostrate hairs of tip.*—Very sparse.

*Density of erect hairs of tip.*—Absent.

Tendrils:

*Length of tendril.*—Very Long, approximately 32.8 cm.

*Color.*—About Yellow-Green 144B and Yellow-Green 144C.

*Thickness.*—Medium to thick.

*Form.*—Usually trifurcated and curled on distil ends.

LEAVES

Young leaves:

*Color of upper surface of first* 4 *distal unfolded leaves.*—About Yellow-Green 144B.

*Color of lower surface.*—About Yellow-Green 146D.

*Average intensity of anthocyanin coloration of six distal leaves prior to flowering.*—Absent.

*Density of erect hairs between veins at lower surface of* 4*th distal unfolded leaf.*—Sparse.

Mature leaves (observations made on leaves in the middle third of shoot):

*Number of lobes*.—Approximately 5.
*Petiole sinus limited by veins*.—Absent.
*Upper surface color*.—About Green 137A and Green 137B.
*Lower surface color*.—About Yellow-Green 144B.
*Shape of blade*.—Pentagonal.
*Arrangement of lobes of petiole sinus*.—Slightly open.
*Length of teeth*.—Long.
*Shape of teeth*.—One side concave and one side convex.
*Density of prostrate hairs between veins on lower side of blade*.—Absent.
*Density of erect hairs on main veins on lower side of blade*.—Sparse.

Lower leaf surface:
*Glossiness*.—Weak.
*Surface appearance*.—Dull.
*Anthocyanin coloration of main veins*.—Absent or very sparse.

Petiole:
*Length of petiole compared to middle vein*.—Moderately shorter.
*Density of prostrate hairs on petiole*.—Sparse.
*Density of erect hairs on petiole*.—Absent.

Buds:
*Time of bud burst*.—Late for the Republic of Korea. Approximately May 3rd.

FLOWERS

General:
*Flower type*.—Fully developed stamen and fully developed gynoecium.
*Time of full bloom*.—Approximately June 8th.
*Opened flower, color of pollen*.—About Yellow 5C.
*Opened flower, color of pistil*.—About Yellow-Green 144B.
*Length of first inflorescence*.—Long.
*Number of inflorescence per flowering shoot*.—Approximately 1.2 to 2.

Peduncle:
*Average length*.—Approximately 4.3 cm.
*Color*.—About Yellow-Green 150B.

Pedicel:
*Average length*.—Approximately 10.1 mm.
*Average diameter*.—Approximately 1.8 mm.

FRUIT

General:
*Ripening period*.—Late, about October 1st.
*Use*.—Fresh market.
*Keeping quality*.—Good.
*Shipping quality*.—Good.
*Date of first harvest*.—About October 1$^{st}$.
*Solid sugar*.—High.
*Refractometer test*.—About 18.4° Brix.
*Tendency to crack*.—Less.

Cluster:
*Form*.—Conical.
*Cluster size (peduncle excluded)*.—Large.
*Cluster length (peduncle excluded)*.—Long, approximately 224.0 cm.
*Cluster average diameter*.—Approximately 14.7 cm.
*Cluster weight*.—High, approximately 538 g.
*Cluster density*.—High.

Berry:
*Size*.—Medium. Average length: Approximately 19.07 mm. Average diameter: Approximately 18.64 mm.
*Uniformity of size*.—Uniform.
*Shape*.—Ovoid.
*Skin color (without bloom)*.—About Greyed-Purple 187B and Greyed-Purple 187C.
*Flesh color*.—Generally translucent. No anthocyanin present.
*Berry firmness*.—Medium.
*Particular flavor*.—Slightly muscat.
*Average weight*.—Approximately 5.4 g.
*Average number per cluster*.—Approximately 100 berries.

Skin:
*Skin texture*.—Smooth.

Seeds:
*Number of seeds per berry*.—On average two stenospermocarpic seeds (seed traces).

Seed traces:
*Number of seed traces per berry*.—Two.
*Average weight*.—1.5 mg.
*Average size*.—6.7 mm long by 3.4 mm wide.

What is claimed is:

1. A new and distinct variety of grapevine as herein illustrated and described.

* * * * * scale bar = 1 cm